United States Patent [19]

Chen

[11] Patent Number: 5,399,176
[45] Date of Patent: Mar. 21, 1995

[54] DISPOSABLE DIAPER WITH LONGITUDINAL ANTI-LEAKAGE MEANS

[75] Inventor: Yu-Ren Chen, Chungli, Taiwan, Prov. of China

[73] Assignee: Fu Burg Industrial Co., Ltd., Taipei, Taiwan, Prov. of China

[21] Appl. No.: 214,670

[22] Filed: Mar. 18, 1994

Related U.S. Application Data

[63] Continuation-in-part of Ser. No. 988,168, Dec. 9, 1992, abandoned.

[51] Int. Cl.$^6$ .............................................. A61F 13/15
[52] U.S. Cl. ............................... 604/385.1; 604/349; 604/385.2
[58] Field of Search ............... 604/346, 349, 350, 351, 604/358, 385.1, 385.2

[56] References Cited

U.S. PATENT DOCUMENTS

| | | | |
|---|---|---|---|
| 4,661,102 | 4/1987 | Shikata et al. | 604/385.2 |
| 4,704,116 | 11/1987 | Enloe | 604/385.2 |
| 4,710,189 | 12/1987 | Lash | 604/385.2 |
| 4,718,901 | 1/1988 | Singheimer | 604/385.2 |
| 4,743,246 | 5/1988 | Lawson | 604/385.2 |
| 4,808,177 | 2/1989 | Des Marais et al. | 604/385.1 |
| 4,816,025 | 3/1989 | Foreman | 604/385.2 |
| 4,895,568 | 1/1990 | Enloe | 604/385.2 |
| 5,037,413 | 8/1991 | Haque | 604/385.1 |
| 5,061,261 | 10/1991 | Suzuki et al. | 604/385.2 |

*Primary Examiner*—Randall L. Green
*Assistant Examiner*—Rob Clarke
*Attorney, Agent, or Firm*—Ostrolenk, Faber, Gerb & Soffen

[57] ABSTRACT

A disposable diaper includes a fluid-impermeable backing layer having a pair of opposite enlarged ends and an intermediate narrowed portion integrally formed therebetween. An absorbent core has a size that is smaller than and in conformity with the size of the backing layer. The absorbent core is disposed at one side on an inner surface of the backing layer. An adhesive unit is disposed at an outer surface of the backing layer. A fluid-permeable facing layer is positioned on the other side of the absorbent core and encompasses the absorbent core. The facing layer is provided with a pair of longitudinal hollow members which extend along the length of the disposable diaper. The facing layer is attached at an edge other than the edge portion forming the hollow members to a corresponding edge of the backing layer. A plurality of elastic elements are received within and are secured to a middle portion of each of the hollow members. The hollow members stand upright due to the longitudinal gathering force that is created by the elastic elements to serve as liquid barriers so as to provide an enhanced anti-leakage effect.

4 Claims, 4 Drawing Sheets

DISPOSABLE DIAPER WITH LONGITUDINAL ANTI-LEAKAGE MEANS

This is a continuation-in-part of application Ser. No. 07/988,168, filed Dec. 9, 1992, now abandoned.

BACKGROUND OF THE INVENTION

1. Field of the Invention

The present invention relates generally to disposable diapers, and more particularly to a disposable diaper with longitudinal anti-leakage means.

2. Description of the Related Art

Referring to FIG. 1, a conventional disposable diaper is shown to comprise a fluid-impermeable backing layer 11, an absorbent core 12, a fluid-permeable facing layer 13, a tape-receiving strip 14, a pair of elasticized anti-leakage portions 15, and two pairs of adhesive tapes 17. In the aforesaid disposable diaper, the absorbent core 12 is disposed between the backing layer 11 and the facing layer 13. The backing layer 11 is attached to the facing layer 13 at the portions surrounding the absorbent core 12 by means of a well known technology, such as by gluing and by heat bonding. The anti-leakage portions 15 are respectively disposed at the middle of laterally opposite side margins of the diaper and are formed by locating longitudinally a plurality of elastic elements 151 at the anti-leakage portions 15 and between the backing layer 11 and the facing layer 13, such that the anti-leakage portions 15 may be contracted by the longitudinal gathering force that is created by the elastic elements 151 in order to serve as anti-leakage barriers. Referring to FIG. 2, in order not to have the full length of the diaper contracted by the longitudinal gathering force that is created by the elastic elements 151, the elastic elements 151 are merely secured at their middle portions 101 to the corresponding anti-leakage portions 15, and the remaining portions thereof are not attached to either the backing layer 11 or the facing layer 13. Therefore, two pairs of tunnel-like channels 16 for respectively receiving the remaining portions of the elastic elements 151 are formed undesirably between the backing layer 11 and the facing layer 13 such that the urine in the absorbent core 12 is susceptible to leaking out of the diaper through the channels 16.

In summary, the aforesaid conventional disposable diaper has the following disadvantages:

1. The conventional disposable diaper does not have a proper structure to locate the male sex organ. In order to prevent the possible leakage caused by the misplacement of the male sex organ, the width W of the diaper is extended at a portion between the legs of the wearer. However, in practical use, the widened portion of the diaper will be unavoidably squeezed by the legs of the wearer, thus making the wearer feel uncomfortable. The possibility of lateral leakage is increased.
2. The conventional disposable diaper provides plane-type anti-leakage portions 15 which are conformed to the wearer's body through the aid of the gathering force that is created by the elastic elements 151 so as to serve as liquid barriers. However, the anti-leakage effect thus obtained is not satisfactory, since the plane-type anti-leakage portions 15 are formed by extending the same outwardly from the diaper, and thus, such an arrangement will undesirably increase the width of the diaper in a portion between the legs of the wearer.
3. The conventional disposable diaper fails to provide a proper structure to locate the male sex organ. Accordingly, because of the direct contact of the sex organ with the urine that was not fully absorbed by the absorbent core 12, the wearer's sex organ will easily develop diaper rash or the like.
4. The conventional disposable diaper unavoidably has two pairs of channels 16 which are in communication with the absorbent core 12. Thus, the urine in the absorbent core will easily leak out of the diaper through the channels 16.
5. Due to the widened portion between the legs of the wearer, the wearer must utilize at least two pairs of adhesive tapes to secure the conventional disposable diaper in position. Therefore, such a diaper is inconvenient for practical use.

SUMMARY OF THE INVENTION

It is the object of the present invention to provide a disposable diaper which comprises a fluid-impermeable backing layer having a pair of opposite enlarged ends and an intermediate narrowed portion integrally formed therebetween. An absorbent core having a size smaller than and in conformity with the size of the backing layer, is disposed at one side on an inner surface of the backing layer. Adhesive means is disposed at an outer surface of the backing layer. A fluid-permeable facing layer is positioned on the other side of the absorbent core and, encompassing the absorbent core. The facing layer is provided with a pair of longitudinal hollow members extending along the length of the disposable diaper, and is attached at an edge other than the edge portion forming the hollow members to a corresponding edge of the backing, layer. A plurality of elastic elements are received within and secured to a middle portion of each of the hollow members, whereby the hollow members may stand upright due to the longitudinal gathering force created by the elastic elements to serve as liquid barriers so as to provide an enhanced anti-leakage effect.

It is another object of the present invention to provide a disposable diaper in which the hollow members of the facing layer are used to receive the elastic elements, thereby eliminating the need to position the elastic elements between the backing layer and the facing layer, so as to alleviate the leakage problems of the conventional disposable diaper.

It is still another object of the present invention to provide a disposable diaper in which a positioning thin member is disposed between the hollow members of the facing layer of the diaper so as to properly locate the male sex organ, the male sex organ being inserted between the facing layer and the positioning member, the positioning member having dimensions adequate to accommodate the male sex organ, the male sex organ being inserted between the facing layer and the positioning member, the positioning member having dimensions adequate to accomodate the male sex organ.

It is a further object of the present invention to provide a disposable diaper in which the adhesive means comprises a pair of adhesive tapes and a tape-receiving member to which the adhesive tapes may be detachably attached.

Other features and advantages of the present invention will become readily apparent from the following detailed description, the accompanying drawings, and the appended claims.

DETAILED DESCRIPTION OF THE PREFERRED EMBODIMENTS

Figure 3:
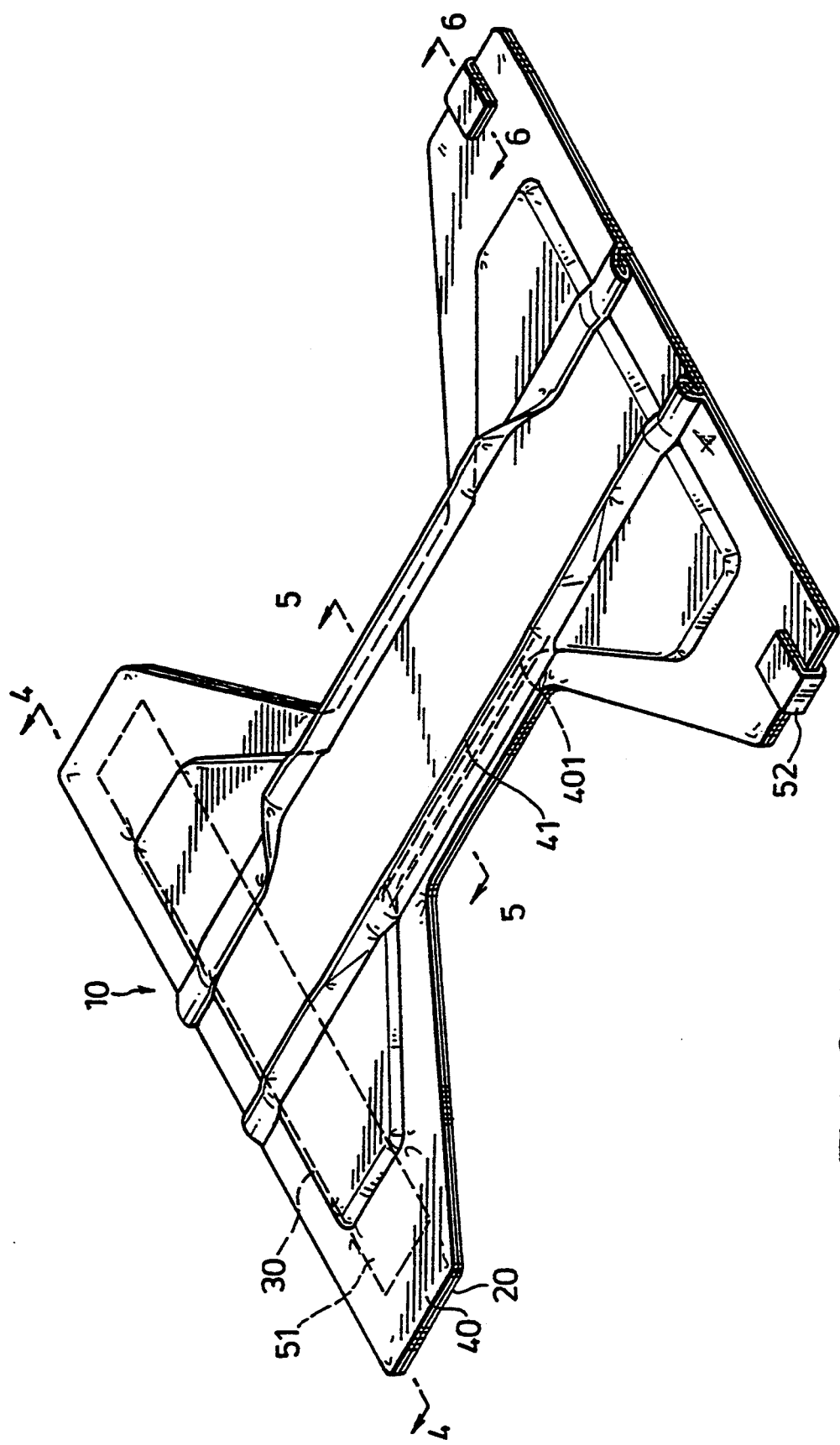
FIG. 3 is a perspective view showing a disposable diaper according to the present invention.
Figure 4:
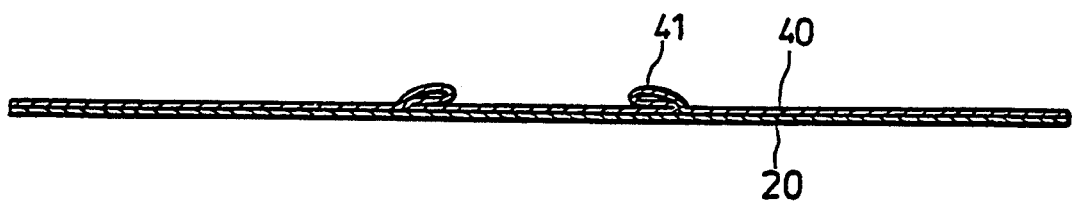
FIG. 4 is a cross-sectional view taken generally along lines 4—4 of FIG. 3.
Figure 5:
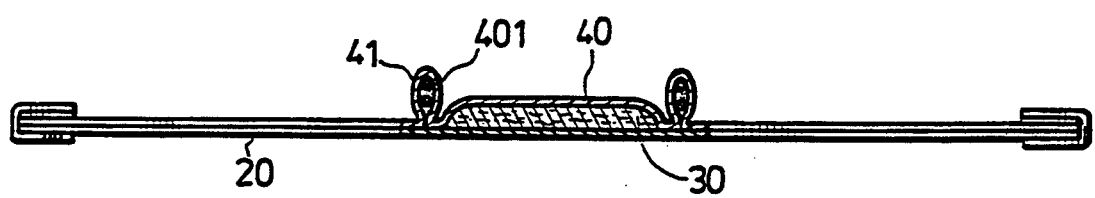
FIG. 5 is a cross-sectional view taken generally along lines 5—5 of FIG. 3.

Referring to FIGS. 3 to 6, a disposable diaper 10 embodying the principles of the present invention is illustrated. The diaper 10 mainly comprises a fluid-impermeable backing layer 20, an absorbent core 30, a fluid-permeable facing layer 40, and a set of adhesive means 51 and 52. The backing layer 20 has a pair of opposite enlarged ends and an intermediate narrowed portion integrally formed therebetween. The backing layer 20 can be formed with plastic materials or any other substantially fluid-impermeable materials. The absorbent core 30, which has a size that is smaller than and in conformity with the size of the backing layer 20, is attached to the inner surface of backing layer 20. The absorbent core 30 can be formed with absorbent wood pulp or other suitable absorbent materials. The facing layer 40 is provided with a pair of longitudinal anti-leakage members 41 which extend to the ends and along laterally opposite side margins of the diaper 10. In a preferred embodiment of the present invention, as illustrated in FIG. 3, the member 41 is shaped into a hollow tubular form by properly folding a predetermined portion of the facing layer 40. The facing layer 40 encompasses the absorbent core 30 and is attached impermeably at an edge other than the edge portion forming the members 41 to a corresponding edge of the backing layer 20 by means of gluing, heat bonding or by any other suitable bonding technology. A plurality of elastic elements 401 are received within and are secured to the middle portion of each member 41 in such a manner that the elastic elements 401 are subject to tension and are extended to a length which is 2.5 to 3.5 times of its original length. The members 41 will stand upright, owning to the longitudinal gathering force that is created by the elastic elements 401, to serve as liquid barriers. Accordingly, the diaper 10 having such members 41 provides an enhanced anti-leakage effect for the wearer. The adhesive means comprises a pair of adhesive tapes 52 disposed at one end of the outer surface of the backing layer 20, and a tape receiving strip 51 disposed at the other end of the outer surface of the backing layer 20. In use, the adhesive tapes 52 can be attached detachably to the corresponding tape-receiving strip 51 so as to secure the diaper 10 in position.

Figure 7:
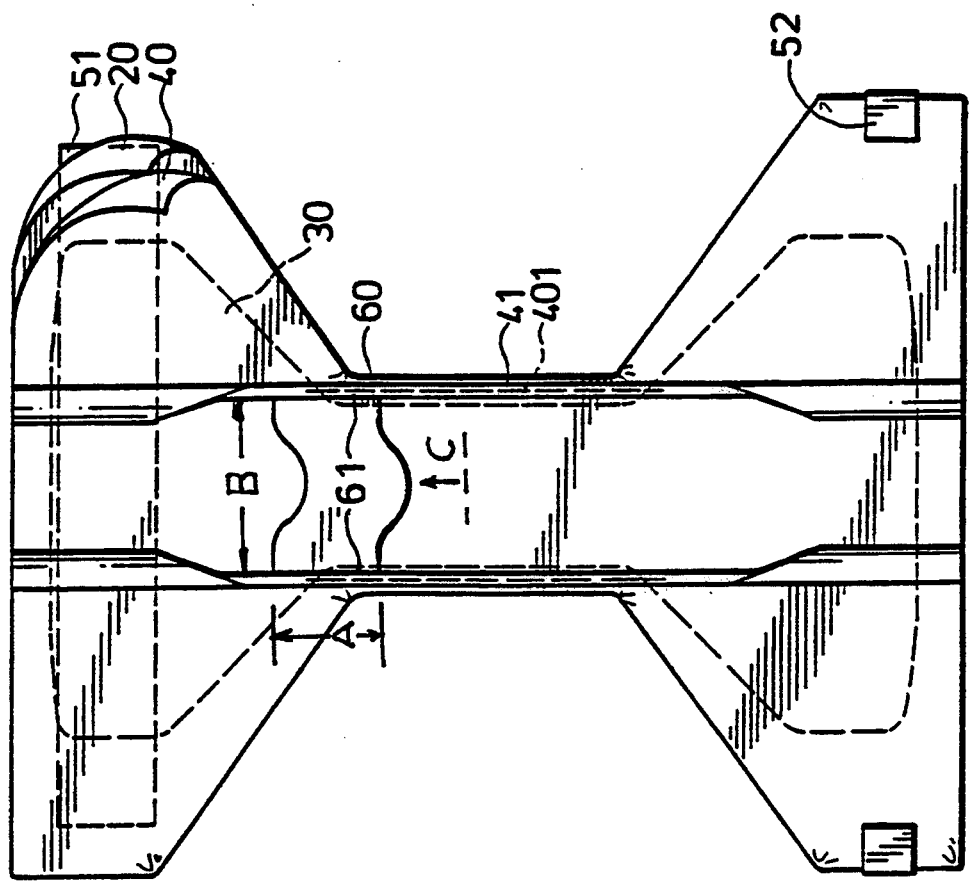
FIG. 7 is a perspective view illustrating another embodiment of a disposable diaper according to the present invention.
Figure 6:
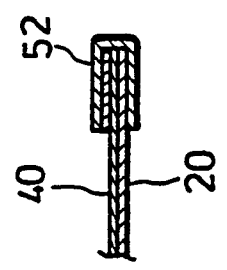
FIG. 6 is a cross-sectional view taken generally along lines 6—6 of FIG. 3.

Referring to FIG. 7, another embodiment of the present invention is illustrated. The diaper as shown further comprises a thin positioning member 60 disposed between the members 41 of the facing layer 40 to properly locate the male sex organ at the central portion of the diaper.

The positioning member 60 extends between the longitudinal hollow members 41 and is attached to members 41 along its side edges, identified in FIG. 7 by reference numeral 61. The male sex organ is inserted and engaged between the positioning member 60 and the facing layer 40.

The positioning member 60 is sized appropriately to accommodate the male sex organ. Specifically, referring to FIG. 7, the two side edges 61 of positioning member 60 have a length A of between 3 cm to 5 cm. The positioning member 60 has a width B (corresponding to the distance between hollow members 41) of between 10 cm to 20 cm. The positioning member 60 is located at an position offset from the center of the diaper by a distance C of between 15 cm to 30 cm. At its midpoint, the positioning member 60 has sufficient slack such that it can be raised from the surface of the facing layer 40 by a distance of between 3 cm to 4 cm to accommodate the male sex organ. The diaper having such a positioning member 60 may keep the male wearer's sex organ dry and can avoid any lateral leakage caused by the misplacement of the sex organ.

Figure 1:
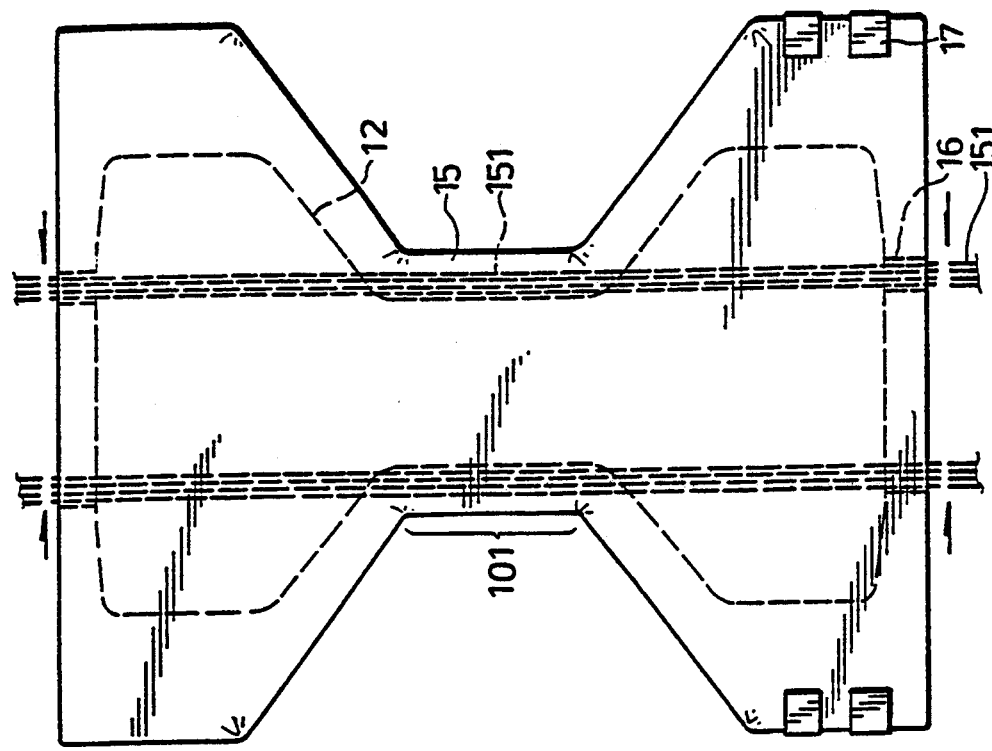
FIG. 1 is a perspective view showing a conventional disposable diaper.
Figure 2:
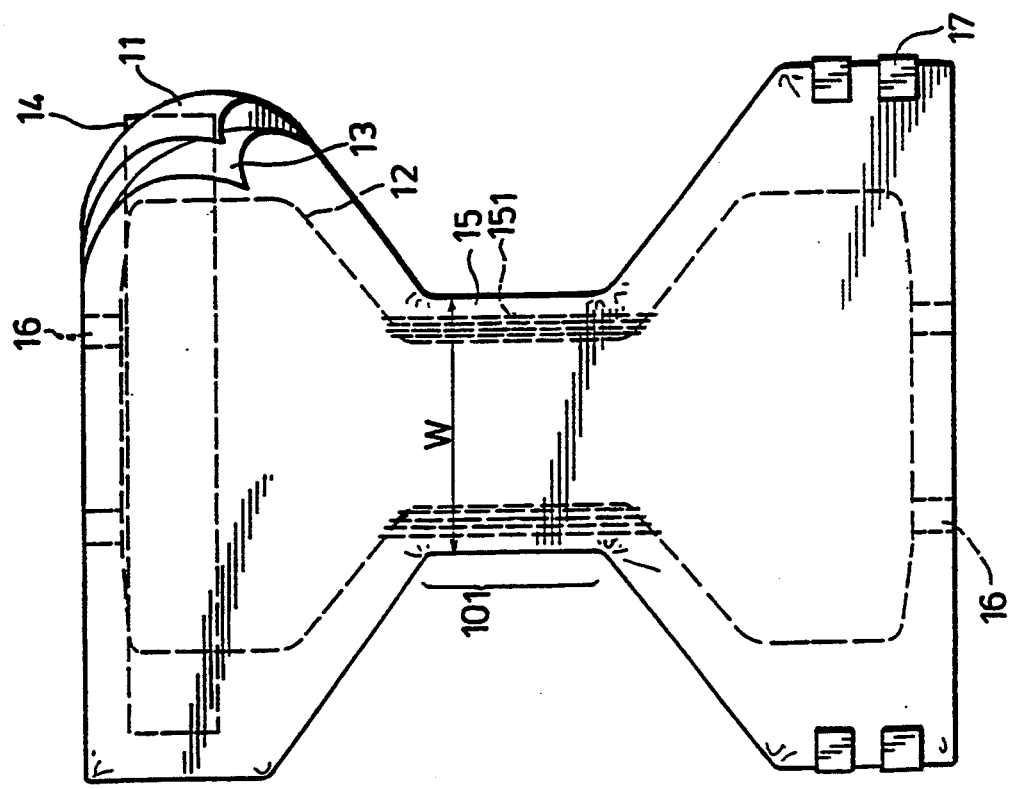
FIG. 2 is a schematic view illustrating the process for manufacturing the diaper of FIG. 1.

In conclusion, the advantages of the present invention can be summarized as follows:

1. The anti-leakage members 41 of the present invention can provide an excellent anti-leakage effect.
2. The anti-leakage members 41 of the present invention are designed to stand upright by means of the longitudinal gathering force created by the elastic elements 401. Therefore, this arrangement may eliminate the necessity of widening the diaper in a portion between the legs of the wearer, thus providing the wearer with better comfort, improved fit, and reliable anti-leakage effect.
3. The positioning member 60 of the present invention can offer the male sex organ a better location and proper protection.
4. The present invention, unlike the conventional disposable diaper as shown in FIG. 2, does not have any channels 16 in communication with the absorbent core 12. Instead, the edge of the backing layer 20 and that of the facing layer 40 of the present invention are sealed together impermeably. Therefore, the present invention may provide a more reliable anti-leakage effect as compared to the conventional one.
5. The present invention can be formed in a more compact form than that of the conventional disposable diaper since no portion of the present diaper needs to be widened so as to provide a better anti-leakage effect. Accordingly, the present diaper merely needs a single pair of adhesive tapes to secure the diaper in position. Such an arrangement could make the wearer feel more convenient and comfortable.

From the foregoing, it will be understood that numerous modifications, variations, and substitutions can be effected without departing from the spirit and scope of the present invention. It is to be noted that no limitation with respect to the specific embodiments illustrated herein is intended. The disclosure is intended to be covered by the appended claims and all such modifications, variations, and substitutions shall fall within the scope of the claims.

I claim:

1. A disposable diaper, comprising:

a fluid-impermeable backing layer having opposed inner and outer surfaces, a pair of opposite enlarged ends, and an intermediate narrowed portion integrally formed between the ends;

an absorbent core having a size smaller than the size of said backing layer, and having a shape conforming with the shape of said backing layer, said absorbent core having opposed sides, one side being disposed on the inner surface of said backing layer;

adhesive means disposed on the outer surface of said backing layer;

a fluid-permeable facing layer positioned on the other side of said absorbent core and encompassing said absorbent core, said facing layer being provided with a pair of longitudinal hollow members extending along an entire length of the disposable diaper, and said facing layer being bonded to said backing layer at portions surrounding said absorbent core;

a plurality of elastic elements received within and secured to a middle portion of each of said hollow members, whereby said hollow members stand upright due to a longitudinal gathering force created by said elastic elements to serve as liquid barriers, so as to provide an enhanced anti-leakage effect; and a positioning member disposed over said facing layer between said hollow members, wherein the sex organ of a male user is inserted between said facing layer and said positioning member to engage and position the male sex organ and keep the organ dry.

2. The disposable diaper as claimed in claim 1, wherein said adhesive means comprises a pair of adhesive tapes and a tape-receiving member to which said adhesive tapes are detachably attached.

3. The disposable diaper as claimed in claim 1, wherein said positioning member has side edges aligned with said hollow members, said side edges having a length of between 3 cm to 5 cm.

4. The disposable diaper as claimed in claim 1, wherein said positioning member has a width between said hollow members of between 10 cm to 20 cm.

* * * * *